United States Patent
Fleig et al.

(10) Patent No.: US 12,262,959 B2
(45) Date of Patent: Apr. 1, 2025

(54) METHOD FOR DETERMINING THE SPATIAL POSITION OF OBJECTS

(71) Applicant: Brainlab AG, Munich (DE)

(72) Inventors: Oliver Fleig, Munich (DE); Timo Neubauer, Munich (DE); Mario Schubert, Munich (DE); Sabine Kling, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 18/240,867

(22) Filed: Aug. 31, 2023

(65) Prior Publication Data
US 2023/0404680 A1 Dec. 21, 2023

Related U.S. Application Data

(63) Continuation of application No. 15/126,425, filed as application No. PCT/EP2014/059870 on May 14, 2014, now abandoned.

(51) Int. Cl.
*A61B 34/20* (2016.01)
*A61B 90/50* (2016.01)

(52) U.S. Cl.
CPC ...... *A61B 34/20* (2016.02); *A61B 2034/2048* (2016.02); *A61B 2034/2051* (2016.02);
(Continued)

(58) Field of Classification Search
CPC ............ A61B 34/20; A61B 2034/2048; A61B 2034/2051; A61B 2034/2055; A61B 2034/2063; A61B 2090/502
See application file for complete search history.

(56) References Cited

U.S. PATENT DOCUMENTS

| | | |
|---|---|---|
| 6,122,538 A | 9/2000 | Sliwa, Jr. et al. |
| 7,966,269 B2 | 6/2011 | Bauer et al. |
| | (Continued) | |

FOREIGN PATENT DOCUMENTS

| | | |
|---|---|---|
| DE | 4225112 C1 | 12/1993 |
| WO | 01/34050 A2 | 5/2001 |
| | (Continued) | |

OTHER PUBLICATIONS

International Search Report, PCT/EP2014/059870 date of mailing Jan. 15, 2015, pp. 1-3.

*Primary Examiner* — Sean A Frith
(74) *Attorney, Agent, or Firm* — Tucker Ellis LLP

(57) ABSTRACT

The present invention relates to a method for determining the spatial position of objects, in particular medical objects. First position data is acquired that describes a spatial position of an object in a first coordinate system. First transformation data is acquired that transforms the object's position from the first coordinate system to a second coordinate system. Based on the foregoing data, second position data is acquired that specifies the spatial position of the object in the second coordinate system. Second transformation data is acquired that transforms the object's position from the second coordinate system to an inertial coordinate system. Based on the second position data and the second transformation data, inertial position data is determined that specifies a position of the object in the inertial coordinate system.

16 Claims, 1 Drawing Sheet

(52) U.S. Cl.
CPC ............... *A61B 2034/2055* (2016.02); *A61B 2034/2063* (2016.02); *A61B 2090/502* (2016.02)

(56) References Cited

U.S. PATENT DOCUMENTS

| | | | |
|---|---|---|---|
| 9,311,883 B2 * | 4/2016 | Cajigas | G02B 27/0172 |
| 2003/0227470 A1 * | 12/2003 | Genc | G06F 3/017 |
| | | | 345/633 |
| 2008/0228422 A1 * | 9/2008 | Satoh | G06F 3/038 |
| | | | 702/92 |
| 2011/0320153 A1 * | 12/2011 | Lightcap | G01C 21/166 |
| | | | 702/94 |
| 2012/0086953 A1 | 4/2012 | Faul et al. | |
| 2012/0224070 A1 | 9/2012 | Burroff et al. | |
| 2013/0267838 A1 * | 10/2013 | Fronk | A61B 5/064 |
| | | | 600/424 |
| 2014/0171785 A1 | 6/2014 | Zino et al. | |

FOREIGN PATENT DOCUMENTS

| | | |
|---|---|---|
| WO | 2007014470 A2 | 2/2007 |
| WO | 2010037436 A1 | 4/2010 |
| WO | 2011/020505 A1 | 2/2011 |

\* cited by examiner

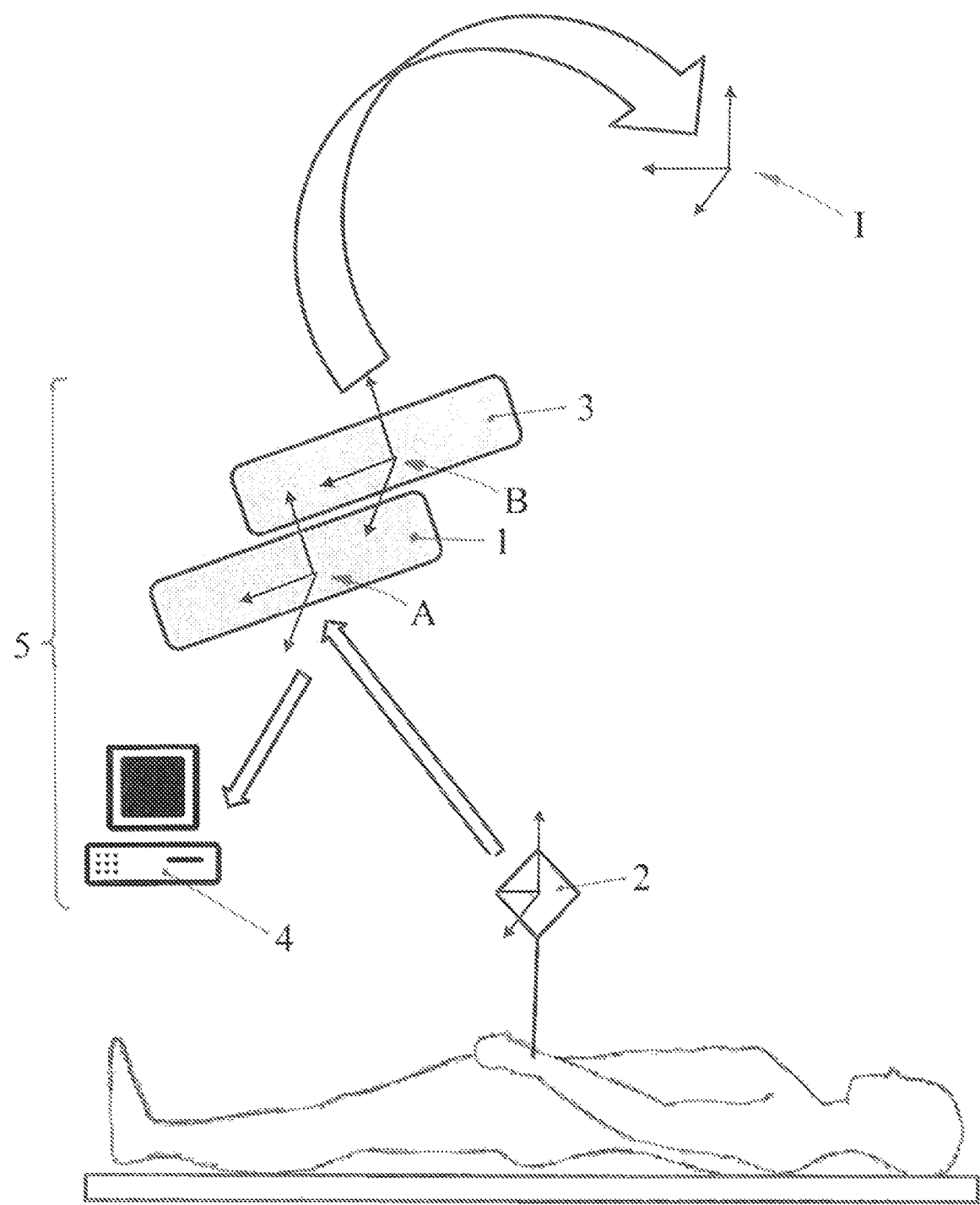

METHOD FOR DETERMINING THE SPATIAL POSITION OF OBJECTS

RELATED APPLICATION DATA

This application is a continuation of U.S. patent application Ser. No. 15/126,425, filed on Sep. 15, 2016. Application Ser. No. 15/126,425 is national phase application of International Application No. PCT/EP2014/059870 filed May 14, 2014 and published in the English language.

The invention relates to the general technical field of determining the spatial position of objects in a medical environment. In medical procedures such as image-guided surgery (IGS), it is desirable to know the spatial position (spatial location and/or spatial orientation) of objects such as medical instruments and devices, as well as anatomical structures of a patient who is to be treated. The spatial position of a medical instrument or a medical device relative to an anatomical structure can for example be determined in order to provide medical staff with a virtual representation of the medical instrument or device and the anatomical structure in their correct spatial relationship, such that a medical procedure can be carried out on the patient with the aid of image guidance.

For this purpose, medical tracking systems are used which are configured to determine the spatial position of objects provided with trackable tracking markers, and which provide a medical navigation system with the corresponding data, such that the tracked objects can ultimately be visualised to medical staff in the correct position relative to each other by means of a display device such as a computer monitor.

Optical navigation systems are a specific type of navigation system which usually comprise a camera array, a computer and a display, wherein all of these components have to be located within the operating theatre. The camera array is configured to determine the position of objects such as surgical instruments which have detectable tracking markers, in particular a so-called reference star, attached to them. In order to track an object over time, its spatial position has to be determined at different points in time relative to a common reference co-ordinate system, for reference purposes, and stored. Such a reference co-ordinate system is usually established by a so-called reference array, the position of which can also be determined with the aid of the camera array. It is therefore necessary to simultaneously detect the position of both the object to be tracked and the reference array which may be provided within the operating theatre at an expedient position, for example on the operating table or on an anatomical structure. Data concerning the instrument position and the reference array position are determined for each point in time, for example with respect to a reference co-ordinate system assigned to the reference array, and stored. DE 196 396 15 shows a neuronavigation system for surgery, comprising a reference array with optically detectable markers which reflect infrared light.

However, as the number of surgical instruments to be tracked by an optical tracking system increases, so too does the issue of "line of sight". This because a permanent line of sight to the markers of each of the objects to be tracked and also to the reference array has to be ensured, which however becomes increasingly difficult to maintain as the number of objects increases.

One problem to be solved by the invention is therefore that of providing a method for determining the spatial position of objects, in particular within a surgical environment, which at least partially overcomes the problems of the prior-art tracking and navigation systems, in particular the problems arising from line-of-sight issues in connection with optical tracking systems.

This problem is solved by the subject-matter of any appended independent claim. Advantages, advantageous features, advantageous embodiments and advantageous aspects of the present invention are disclosed in the following and contained in the subject-matter of the independent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

In accordance with the present invention, a method for determining the spatial position of objects, in particular medical objects, comprises the following steps:

acquiring first position data which comprise first position information describing the spatial position of an object within a first co-ordinate system;

acquiring first transformation data which comprise first transformation information describing a transformation of the object's position from the first co-ordinate system into a second co-ordinate system;

acquiring, on the basis of the first position data and the first transformation data, second position data which comprise second position information describing the spatial position of the object within the second co-ordinate system;

acquiring second transformation data which comprise second transformation information describing a transformation of the object's position from the second co-ordinate system into an inertial co-ordinate system;

determining, on the basis of the second position data and the second transformation data, inertial position data which comprise inertial position information describing the spatial position of the object within the inertial co-ordinate system.

Within the framework of the present invention, the term of spatial position encompasses in particular at least one of spatial location and spatial orientation. For certain applications, such as for example determining the inertial position data on the basis of the second position data and the second transformation data within the method outlined in the preceding paragraph, it can be sufficient to consider preferably the spatial orientation. In particular, the first position data and the second position data describe (in particular define) the spatial orientation of object. In particular, the position of the object is understood to be defined by preferably (only) the orientation of the object. It is not necessary to have knowledge of the location (i.e. the three-dimensional coordinates at which the object is located) of the object. Rather, it will be sufficient to have knowledge of the orientation (i.e. the spatial alignment which may be defined by angular values in a three-dimensional—e.g. angular—co-ordinate system) of the object.

In the framework of the present invention, the terms "spatial position", "spatial location" and "spatial orientation" are also called merely "position", "location" and "orientation", respectively, without using the adjective "spatial", however with the same meaning as if the adjective "spatial" were used.

The present invention is described in other terms in the following paragraph, wherein this concise description is however to be considered merely as an example and in no way limits the invention to the features described in said paragraph.

The present invention provides a method for determining the spatial position of medical objects such as surgical instruments and anatomical structures, both of which are provided with tracking markers, wherein the position of each of the tracking markers and therefore each of the corresponding objects is determined by means of a tracking sensor array, in particular a tracking camera array comprising one or more cameras, configured to detect tracking markers attached to the objects to be tracked. Data concerning the position of each of the objects are initially determined by the tracking sensor array with reference to the tracking sensor co-ordinate system and then transformed into data describing the position of each of the objects with respect to a co-ordinate system assigned to an inertial sensor array which is fixed to the tracking sensor array and therefore capable of detecting any movement of the tracking sensor array with respect to the "global co-ordinate system" which is invariant over time. By transforming the data, considering a possible movement of the tracking sensor array and storing the positional data with respect to the global co-ordinate system or inertial co-ordinate system for each of the tracked objects, the inertial co-ordinate system acts as a centre of reference, thereby enabling a comparison of the relative position of the tracked objects over time, even when the tracking sensor array together with the tracking sensor co-ordinate system assigned to it is moved relative to the surgical environment, and even without any additionally provided tracking reference as known from the prior art.

In accordance with one preferred embodiment of the present invention, the first position data are acquired by means of a medical tracking system comprising a (tracking) sensor array configured to determine the spatial position of at least one tracking marker which is attached to an object to be tracked, wherein the first co-ordinate system is in particular positionally assigned to said sensor array.

Such a sensor array can in particular comprise any kind of sensor(s) which can be used to determine the position of tracking markers attached to the object to be tracked. Feasible tracking sensors include for example optical cameras, which can also include cameras which are sensitive to infrared light, EM (electromagnetic) tracking sensors and ultrasound tracking sensors.

Although most aspects of the present invention are described here in connection with an optical tracking system comprising one or more optical tracking cameras, any kind of non-optical tracking system may also benefit from the present invention. The tracking sensor array can for example be rendered movable or even portable and can therefore be placed nearer to the objects to be tracked, which can increase its accuracy during the tracking procedure. A tracking reference which acts as a centre of reference, and which is therefore an essential component of conventional tracking systems with movable tracking sensors, is not however needed in accordance with the present invention, since the position of the tracked objects is determined with respect to an inertial co-ordinate system which remains invariant over time.

The inertial co-ordinate system can for example be positionally assigned to a treatment room which accommodates the treatment/surgical set-up. In other words, the inertial co-ordinate system is a "global co-ordinate system" which is invariant with respect to the operating theatre.

The second co-ordinate system can also be positionally assigned to (i.e. positionally invariant with respect to) an inertial sensor array which is fixedly attached to the medical tracking system's sensor array and configured to sense any motion of the medical tracking system's sensor array within the inertial co-ordinate system, wherein the second co-ordinate system in particular corresponds to the first co-ordinate system. An expedient inertial sensor array can comprise at least one sensor selected from the group consisting of:
  accelerometers,
  sensors or sensor arrangements which are configured to be sensitive to the earth's gravitational field;
  magnetometers;
  gyroscopes;
  optical cameras, in particular cameras which are sensitive to infrared light;
  pressure sensors which are sensitive to atmospheric pressure.

Currently available inertial sensors may be used to precisely determine the spatial orientation of the object in the inertial co-ordinate system. Determination of the exact three-dimensional spatial location is however also basically achievable from the viewpoint of physics. In the framework of the present invention, it is sufficient to determine the spatial orientation, exact knowledge about the three-dimensional location of the object is not necessary to carry out the present invention.

The transformations applied in the framework of the present invention (in particular the transformation of the object's position from the second co-ordinate system into the inertial co-ordinate system) therefore comprise at least one of the following:
  a rotational transformation (in three rotational degrees of freedom) from the second co-ordinate into the inertial co-ordinate system, which transformation is usable to determine the spatial orientation of the object in the inertial co-ordinate system;
  a complete transformation (in three rotational degrees of freedom and three translational degrees of freedom) from the second co-ordinate system into the inertial co-ordinate system, which transformation is usable to determine the complete spatial position (i.e. both the spatial location and the spatial orientation) of the object in the inertial co-ordinate system.

The second co-ordinate system assigned to the inertial sensor array does not necessarily have to be different to the first co-ordinate system assigned to the tracking sensor array, but rather can also be identical to it.

In accordance with another preferred embodiment of the present invention, the inertial position data are stored for at least one object and/or anatomical structure and in particular for a plurality of points which are palpated (for example during a point acquisition and registration procedure), wherein the tracked object is a point acquisition instrument, in particular a pointer instrument. Since the positional data for each of the objects/points can be stored over time and therefore compared relative to a common centre of reference, namely the inertial co-ordinate system, an accurate tracking procedure and/or point acquisition procedure is possible even without an invariantly installed camera array and/or additionally provided reference array.

Another aspect of the present invention relates to a program which, when running on a computer, causes the computer to perform the method steps of any embodiment described above and/or to a program storage medium on which the program is stored and/or to a computer comprising such a program storage medium and/or to a signal wave, in particular a digital signal wave, carrying information which represents the program.

A third aspect of the present invention relates to a tracking system which comprises:
- a sensor array which is configured to determine the spatial position of at least one tracking marker attached to an object;
- an inertial sensor array which is attached to said sensor array; and
- a computer which is configured to perform the method steps as described above.

One preferred embodiment of the tracking system in accordance with the invention comprises a freely movable tracking sensor array and a freely movable inertial sensor array attached to it. The tracking sensor array and the inertial sensor array are preferably accommodated in a common unit or housing which is freely movable within the operating theatre and relative to the inertial co-ordinate system. A tracking system in accordance with the present invention can consist of a mobile phone comprising an optical camera which can be used as a tracking sensor array and accelerometers which can be used as inertial sensors.

The common unit which accommodates both the tracking sensor array and the inertial sensor array can be configured so as to be worn by a person, in particular as a device similar to spectacles, and specifically configured to provide the wearer with additional information based on the determined spatial position of the at least one object. One example of such a spectacle-like device which can be used in connection with the present invention is the miniaturised computer Google Glass™ which is worn as a so-called optical head-mounted display. By wearing such a device, surgeons can keep their hands free for other tasks and the tracking sensor array can be automatically positioned right next to the region of interest and/or object to be tracked.

Using such a spectacle-like device, it is for example possible to detect mistakes during a registration procedure and inform the user of the detected problem directly on the device by overlaying the information. Depending on the device used, the information could be overlaid directly onto the surgeon's field of view or onto a video image being displayed within the surgeon's field of view.

There are no sterility issues, since the spectacle-like device is worn, like regular spectacles, on the nose. Unlike existing solutions, it is not necessary to for example drape a monitor in order to press buttons on the monitor, or to drape a smart device in such a way that it can be used within the sterile field.

The terminology used in this document is described in more detail below, wherein this description also forms part of the disclosure of the present invention.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

It is the function of a marker to be detected by a marker detection device (for example, a camera or an ultrasound receiver or analytical devices such as CT or MRI devices) in such a way that its spatial position (i.e. its spatial location and/or orientation/alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block X-ray radiation. To this end, the marker can be provided with a surface which has corresponding reflective properties or can be made of metal in order to block the X-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of the detection points which represent the main points and auxiliary points, in order to generate detection signals and to supply the generated detection signals to the computer, such that the computer can determine the absolute main point data and absolute auxiliary point data on the basis of the detection signals received. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (or World Wide Web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The present invention will work well in connection with tools, particularly tools used in connection with orthopedics of Brainlab®, such as products called "Digital Ortho Tools", which will then give the surgeons the feeling they are working with intelligent tools instead of a complex navigation system. With this invention it is possible to combine inertial sensors with a camera system so that it is not necessary to have an external reference on the table or on the patient and so e.g. additional pins within the patients' bone can be avoided. Additionally line of sight issues as known from the optical tracking system can be reduced significantly as only one reference has to be visible to the camera during the point acquisition. The overall system is more flexible and the workflow of the surgeon is not interrupted by a complex navigation system.

In the following, the invention is described with reference to the one enclosed FIGURE which represents a preferred embodiment of the invention, without the invention being in any way limited to the specific features shown in this FIGURE.

FIG. 1 schematically shows an embodiment of the tracking system in accordance with the present invention.

As is shown in FIG. 1, a tracking camera array 1 is configured to detect the spatial position of a tracking marker array 2 attached to a part of a patient's body (the object to be tracked). The positional data are determined by the camera array 1 with respect to a first co-ordinate system A which is assigned to the camera array 1. The positional data are then transformed into positional data which describe the spatial position of the object with respect to a second co-ordinate system 8 assigned to an inertial sensor array 3 which is fixedly attached to the camera array 1. The inertial sensor array 3 detects any motion of the camera array 1 together with the inertial sensor array 3 with respect to an invariant inertial co-ordinate system I. The positional data are then transformed into data which describe the object's position (in particular its orientation) with respect to the inertial co-ordinate system I. The data which describe the object's position within the inertial co-ordinate system I are then stored by means of a computer 4 for subsequent use, for example during a tracking procedure used to acquire the position of landmarks on a part of the patient's body.

The invention claimed is:

1. A data processing system, comprising at least one computer having at least one processor configured to execute a computer-implemented medical data processing method for determining the spatial position of medical objects in three-dimensional space, the data processing method comprising the steps of:

acquiring, at the processor and via a medical tracking system comprising a sensor array, first position data which comprise first position information describing a three-dimensional spatial position of an object within a first co-ordinate system positionally assigned to said sensor array which is configured to determine the three-dimensional spatial position of at least one tracking marker attached to the object;

acquiring, at the processor, first transformation data which comprise first transformation information describing a transformation of the object's three-dimensional spatial position from the first co-ordinate system into a second co-ordinate system positionally assigned to an inertial sensor array which is attached to the medical tracking system's sensor array and configured to sense any motion of the medical tracking system's sensor array within a treatment room which accommodates the object;

acquiring, at the processor and on the basis of the first position data and the first transformation data, second position data which comprise second position information describing the three-dimensional spatial position of the object within the second co-ordinate system;

acquiring, at the processor, second transformation data which comprise second transformation information describing a transformation of the object's three-dimensional spatial position from the second co-ordinate system into a third co-ordinate system positionally assigned to the treatment room;

determining, by the processor and on the basis of the second position data and the second transformation data, position data which comprise position information describing the three-dimensional spatial position of the object within the third co-ordinate system.

2. A computer implemented medical data processing method for determining the spatial position of medical objects in three-dimensional space, the method comprising executing, on at least one processor of at least one computer, the steps of:

acquiring at the processor and via a medical tracking system comprising a sensor array, first position data which comprise first position information describing a three-dimensional spatial position of an object within a first co-ordinate system positionally assigned to said sensor array which is configured to determine the three-dimensional spatial position of at least one tracking marker attached to the object;

acquiring, at the processor, first transformation data which comprise first transformation information describing a transformation of the object's three-dimensional spatial position from the first co-ordinate system into a second co-ordinate system positionally assigned to an inertial sensor array which is attached to the medical tracking system's sensor array and configured to sense any motion of the medical tracking system's sensor array within a treatment room which accommodates the object;

acquiring, at the processor and on the basis of the first position data and the first transformation data, second position data which comprise second position information describing the three-dimensional spatial position of the object within the second co-ordinate system;

acquiring, at the processor, second transformation data which comprise second transformation information describing a transformation of the object's three-dimensional spatial position from the second co-ordinate system into a third co-ordinate system positionally assigned to the treatment room;

determining, by the processor and on the basis of the second position data and the second transformation data, position data which comprise position information describing the three-dimensional spatial position of the object within the third co-ordinate system.

3. The method according to claim 2, wherein the second co-ordinate system is equal to the first co-ordinate system.

4. The method according to any one of claim 2, wherein the inertial position data are stored for at least one object and for a plurality of points which are palpated during a point acquisition and registration procedure, wherein the tracked object is a pointer instrument.

5. A non-transitory computer-readable program storage medium storing a computer program which, when executed on a processor of a computer or leaded into the memory of a computer, causes the computer to perform a computer-implemented medical data processing method for determining the spatial position of medical objects in three-dimensional space, the data processing method comprising the steps of:

acquiring, at the processor and via a medical tracking system comprising a sensor array, first position data which comprise first position information describing a three-dimensional spatial position of an object within a first co-ordinate system positionally assigned to said sensor array which is configured to determine the three-dimensional spatial position of at least one tracking marker attached to the object;

acquiring, at the processor, first transformation data which comprise first transformation information describing a transformation of the object's three-dimensional spatial position from the first co-ordinate system into a second co-ordinate system positionally assigned to an inertial sensor array which is attached to the medical tracking system's sensor array and configured to sense any motion of the medical tracking system's sensor array within a treatment room which accommodates the object;

acquiring, at the processor and on the basis of the first position data and the first transformation data, second position data which comprise second position information describing the three-dimensional spatial position of the object within the second co-ordinate system;

acquiring, at the processor, second transformation data which comprise second transformation information describing a transformation of the object's three-dimensional spatial position from the second co-ordinate system into a third co-ordinate system positionally assigned to the treatment room;

determining, by the processor and on the basis of the second position data and the second transformation data, position data which comprise position information describing the three-dimensional spatial position of the object within the third co-ordinate system.

6. A computer comprising the non-transitory computer-readable program storage medium according to claim 5.

7. A medical tracking system for determining a spatial position of medical objects within a three-dimensional space of a treatment room, comprising:

a sensor array configured to determine a three-dimensional spatial position of an object within a first coordinate system, wherein the first coordinate system is defined relative to the sensor array;

an inertial sensor array configured to detect motion of the sensor array relative to a global coordinate system associated with the treatment room; and a computer having at one processor configured to execute a computer program that configures the processor to:
  acquire, via the sensor array, first position information that indicates the three-dimensional spatial position of the object within the first coordinate system;
  acquire first transformation information that describes a transformation from the first coordinate system to a second coordinate system, wherein the second coordinate system is defined relative to the inertial sensor array;
  transform the three-dimensional spatial position of the object from the first coordinate system to the second coordinate system based on the first position information and the first transformation information;
  acquire second transformation information that describes a transformation from the second coordinate system to the global coordinate system based on motion detected by the inertial sensor array; and
  determine global position information that describes the three-dimensional spatial position of the object within the global coordinate system of the treatment room.

8. The medical tracking system of claim 7, wherein the sensor array and the inertial sensor array are freely movable at least within the treatment room.

9. The medical tracking system of claim 7, further comprising a common unit housing the sensor array and the inertial sensor array.

10. The medical tracking system of claim 9, wherein the common unit is a wearable, spectacle-like device.

11. The medical tracking system of claim 10, wherein the wearable, spectacle-like devices includes a head-mounted display.

12. The medical tracking system of claim 7, wherein the inertial sensor array is attached to sensor array.

13. The medical tracking system of claim 7, wherein the first coordinate system corresponds to the second coordinate system.

14. The medical tracking system of claim 7, wherein the sensor array determines the three-dimensional spatial position of the object within the first coordinate system based on at least one tracking marker attached to the object.

15. The medical tracking system of claim 7, wherein the sensor array comprises at least one sensor selected from the group consisting of:
   an optical camera that is sensitive to infrared light;
   an electromagnetic tracking sensor; or
   an ultrasound tracking sensor.

16. The tracking system of claim 7, wherein the inertial sensor array comprises at least one sensor selected from the group consisting of:
   an accelerometer;
   a sensor or sensor arrangement configured to be sensitive to Earth's gravitational field;
   a magnetometer;
   a gyroscope;
   an optical camera that is sensitive to infrared light; or
   a pressure sensor that is sensitive to atmospheric pressure.

* * * * *